(12) United States Patent
Bridger et al.

(10) Patent No.: US 10,031,256 B2
(45) Date of Patent: Jul. 24, 2018

(54) METHOD OF OPERATING A RADIOGRAPHIC INSPECTION SYSTEM WITH A MODULAR CONVEYOR CHAIN

(71) Applicant: Mettler-Toledo Safeline X-Ray Ltd., Royston, Hertfordshire (GB)

(72) Inventors: Nick Bridger, Northamptonshire (GB); Nigel King, Bedfordshire (GB)

(73) Assignee: METTLER-TOLEDO SAFELINE X-RAY LTD., Hertfordshire (GB)

( * ) Notice: Subject to any disclaimer, the term of this patent is extended or adjusted under 35 U.S.C. 154(b) by 606 days.

(21) Appl. No.: 14/661,615

(22) Filed: Mar. 18, 2015

(65) Prior Publication Data

US 2015/0192690 A1   Jul. 9, 2015

Related U.S. Application Data

(63) Continuation of application No. PCT/EP2013/069586, filed on Sep. 20, 2013.

(30) Foreign Application Priority Data

Sep. 21, 2012 (EP) .................................. 12185507

(51) Int. Cl.
   *G01V 5/00* (2006.01)
   *G01N 23/04* (2018.01)
   *G01T 7/00* (2006.01)

(52) U.S. Cl.
   CPC ........... *G01V 5/0016* (2013.01); *G01N 23/04* (2013.01); *G01T 7/005* (2013.01)

(58) Field of Classification Search
   CPC .. G01N 23/04; G01N 2223/643; G01T 7/005; G01V 5/0016; G06T 2207/10116;
   (Continued)

(56) References Cited

U.S. PATENT DOCUMENTS 4,138,011 A * 2/1979 Lapeyre ................. B65G 17/08
                                                                198/842
4,366,382 A   12/1982 Kotowski
(Continued)

FOREIGN PATENT DOCUMENTS

CN   1276870 A   12/2000
CN   1380544 A   11/2002
(Continued)

OTHER PUBLICATIONS

Office Action (Notice of Reasons for Rejection) dated Feb. 16, 2017, by the Japanese Patent Office in corresponding Japanese Patent Application No. 2015-532425 and English translation of the Office Action. (7 pages).

(Continued)

*Primary Examiner* — Glen Kao
(74) *Attorney, Agent, or Firm* — Buchanan Ingersoll & Rooney PC

(57) ABSTRACT

A method of operating a radiographic inspection system is disclosed for a system in which a conveyor chain with identical modular chain segments transports articles under inspection. Two operating modes of the radiographic inspection system includes a calibration mode in which calibration data characterizing the radiographic inspection system with an empty conveyor chain are generated; and an inspection mode in which raw image data of articles under inspection with the background of the conveyor chain are acquired and arithmetically processed with calibration data into a clearer output image, without the interfering background of the conveyor chain.

20 Claims, 3 Drawing Sheets

(58) Field of Classification Search
CPC . G06T 2207/10121; G06T 2207/30128; G06T 2207/30136; G06T 7/0004; G06T 7/194
See application file for complete search history.

(56) References Cited

U.S. PATENT DOCUMENTS

| | | | |
|---|---|---|---|
| 5,627,910 A | 5/1997 | Gachet et al. | |
| 5,828,724 A * | 10/1998 | Kurtz | G01N 23/20041 378/70 |
| 5,974,111 A | 10/1999 | Krug et al. | |
| 7,980,760 B2 | 7/2011 | Kabumoto et al. | |
| 2006/0078085 A1 | 4/2006 | Zanker | |
| 2007/0012547 A1 * | 1/2007 | DePaso | B65G 43/00 198/810.03 |
| 2010/0002835 A1 | 1/2010 | Kabumoto et al. | |
| 2010/0059681 A1 * | 3/2010 | Nakamura | C09K 11/7774 250/361 R |
| 2012/0128133 A1 * | 5/2012 | King | B65G 17/08 378/208 |

FOREIGN PATENT DOCUMENTS

| | | |
|---|---|---|
| CN | 101495854 A | 7/2009 |
| CN | 102448855 A | 5/2012 |
| EP | 2 045 596 A1 | 4/2009 |
| EP | 2 256 069 A1 | 12/2010 |
| GB | 2 390 005 A | 12/2003 |
| JP | 03-116299 A | 5/1991 |
| JP | 10-062362 A | 3/1998 |
| JP | 2001-004560 A | 1/2001 |
| JP | 2008-026198 A | 2/2008 |
| JP | 2008-122184 A | 5/2008 |
| JP | 2012-528060 A | 11/2012 |
| WO | WO 2009/030923 A1 | 3/2009 |
| WO | 2009/114928 A1 | 9/2009 |
| WO | WO 2009/114928 A1 | 9/2009 |

OTHER PUBLICATIONS

International Search Report (PCT/ISA/210) dated Nov. 22, 2013, by the European Patent Office as the International Searching Authority for International Application No. PCT/EP2013/069586.

European Search Report dated Mar. 4, 2013, for EP Application No. 12185507.

International Preliminary Report on Patentability and the Written Opinion of the International Searching Authority (Forms PCT/IB/373 and PCT/ISA/237) dated Mar. 24, 2015, by the International Bureau of WIPO in corresponding International Application No. PCT/EP2013/069586. (10 pages).

English translation of the Office Action dated Jul. 27, 2016, by the State Intellectual Property Office of China in corresponding Chinese Patent Application No. 201380049149.2. (10 pages).

* cited by examiner

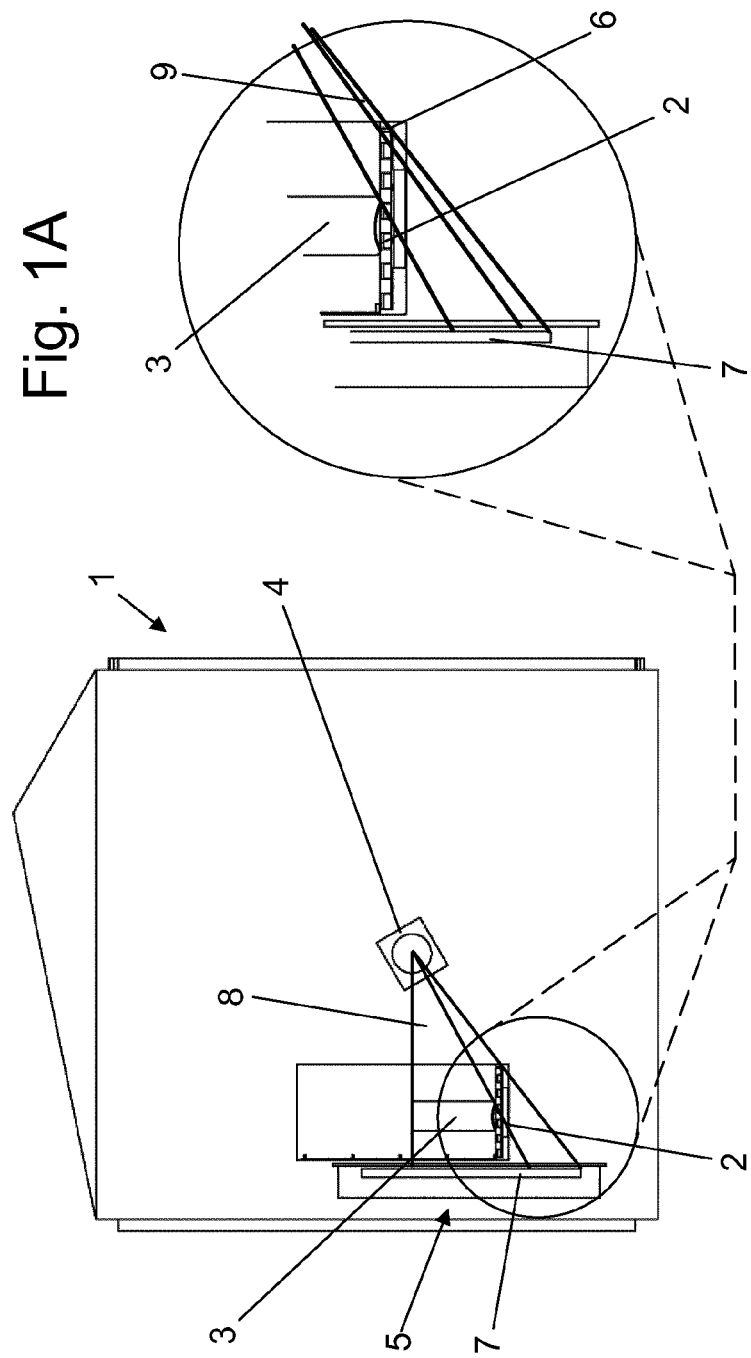

METHOD OF OPERATING A RADIOGRAPHIC INSPECTION SYSTEM WITH A MODULAR CONVEYOR CHAIN

RELATED APPLICATIONS

This application claims priority as a continuation application under 35 U.S.C. § 120 to PCT/EP2013/069586, which was filed as an International Application on Sep. 20, 2013, and which claims priority to European Application 12185507.6 filed in Europe on Sep. 21, 2012. The entire contents of these applications are hereby incorporated by reference in their entireties.

FIELD

The disclosure relates to the field of radiographic inspection systems in which articles under inspection travel on an endless-loop conveyor through an X-ray machine or other radiographic scanner system. For example, a method of operating a radiographic inspection is disclosed in which the endless-loop conveyor is a modular conveyor chain. Systems and methods are disclosed herein for cancelling the effect that transmittance variations of the conveyor chain have on the radiographic image produced by the scanner system.

BACKGROUND INFORMATION

The term "conveyor chain" in the present context refers, for example, to an endless-loop conveyor device analogous to a conveyor belt, but with the difference that a conveyor chain includes a multitude of rigid segments or links which are connected to each other in a closed loop wherein each link is articulately hinged to a following link and a preceding link. The segments can either be all identical to each other, or a group of dissimilar segments can identically repeat itself around the conveyor chain. The individual segment or group of segments that identically repeats itself is referred to herein as a module or as modular segment and, consequently, the conveyor chain is referred to as a modular conveyor chain.

The radiation transmittance of the endless-loop conveyor comes into play in inspection systems whose geometric arrangement is such that at least part of the scanner radiation passes not only through the products under inspection and the air space surrounding them, but also traverses the endless-loop conveyor. This kind of inspection system is used for example for the detection of foreign bodies in bottled or canned food and beverage products. Of particular concern are metal and glass fragments in liquid products. Due to their higher density relative to the liquid, such foreign bodies will collect at the bottom of the container. Furthermore, if the container has a domed bottom, the foreign bodies will tend to settle at the perimeter where the bottom meets the sidewall of the container. It is therefore very important in such systems for the radiographic scanner system to be configured and arranged in relation to the endless-loop conveyor in such a way that an entire inside bottom surface of each container is covered by the scan. Consequently, a scanner arrangement is used where at least part of the radiation passes through the bottom of the container and therefore also through the area of the endless-loop conveyor on which the container or any other object to be inspected is positioned.

In known arrangements, the radiation used for the inspection may for example originate from a radiation source located above the conveyor path, pass at an oblique angle through the sidewall into the container, exit through the container bottom and pass through the conveyor, to be received by a detection system which is connected to an image-processing system. Alternatively, for example when objects are inspected, that are neither bottled nor canned, the radiation source can be arranged vertically above the conveyor and the radiation detector vertically below said conveyor.

If the radiographic inspection system is an X-ray system, the rays can be received for example by an X-ray image intensifier and camera, or by an X-ray line array sensor, or by an X-ray area array sensor, both of which then pass a signal to the image processing system. For example, the imaging radiation originates as a fan-shaped planar bundle of rays from a localized radiation source (e.g., a spot-sized radiation source) and is received by a linear array of photodiodes that are collectively referred to as a radiation detector, wherein the fan-shaped radiation bundle and the linear array of photodiodes lie in a common plane, also referred to as the scanning plane, which runs substantially orthogonal to the travel direction of the conveyor carrying the articles to be inspected. While the articles under inspection move through the scanning plane, the linear array of photodiodes is triggered by a continuous sequence of discrete pulses, and the pulse frequency is coordinated with the speed of the conveyor so that the sequence of signals received by the radiation detector array can be translated into a pattern of raster dots with different brightness values expressed for example in terms of a brightness scale from zero to 255, representing a transparent shadow image of the material bodies between the radiation source and the radiation detector. If a scanned article contains foreign objects such as metal fragments, which have a lower transmittance to the scanning rays than the scanned article, the radiographic image will show such foreign objects as darker areas within the transparent shadow image of the scanned article.

At the present state of the art, endless-loop conveyors that are used as transport devices in radiographic inspection systems are for example, polymer fabric belts. This type of conveyor has an advantage that the quality of the X-ray image is least affected by it, due to the constant thickness and the uniformity of the belt. However, there are a number of strong arguments against polymer fabric belts and in favor of modular conveyor chains, specifically:

There is strong resistance to the use of fabric belts particularly in the bottling and canning industry, because they are easily damaged and wear out rapidly. In comparison, conveyor chains consisting of rigid plastic elements (such as of acetal resin or polypropylene) that are linked together in an endless loop are much stronger and less easily damaged by hard metal or glass containers.

Conveyor chains are better suited for heavy-weight articles such as blocks of cheese, as it is possible to drive the conveyor chain with sprockets that directly engage the chain profile.

The segments of a conveyor chain can be hinged together in such a way that the chain has a unilateral flexibility to loop around the drive sprockets while being rigid against bending in the opposite direction. This latter property eliminates the need for guiding mechanisms which can be unreliable in continuous-duty applications.

Conveyor chains are easier to replace or repair than belts, because the chain can be opened by removing one of the hinge pins by which the modular elements of the chain are linked together.

Conveyor chains can be designed to be self-tracking and to run flush with the sides of the conveyor support structure. This last characteristic can be important, because it can allow products to be easily transferred sideways between laterally adjacent conveyors.

Nevertheless, the use of customary chain conveyors with plastic chain links can be an issue in radiographic inspection systems, because the chain links can interfere with the X-ray image. Until now, if one wished to X-ray a product moving on a conveyor chain, the resultant image was degraded by the variations in the transmittance of the conveyor chain superimposed on the product, for example due to hinges or other connections between the chain segments or by profile features designed to stiffen the chain segments. If this issue of image interference can be solved, the benefits of modular conveyor chains as listed above can be applied to radiographic inspection systems.

In US 2012/0128133 A1, which is owned by the same assignee as the present disclosure, the issue of transmittance variations is solved through a conveyor chain in which the chain segments are configured in essence as rigid plates of uniform thickness and density extending over the width of the conveyor chain, wherein the segments overlap each other to present themselves to the scanner radiation as a substantially gapless band of uniform transmittance and wherein the connectors or hinges which link the segments together (and which have a lower transmittance than the flat areas of the segments) are located outside the band that is traversed by the scanner radiation. Thus, the connections between the segments are for example located in the two lateral border areas of the conveyor chain.

In a conveyor chain according to the foregoing concept, the absence of hinges or any other stiffening features in the central homogeneous band area reduces the rigidity of the chain segments in regard to transverse bending and therefore limits the conveyor width that can be realized in a practical design. A treatment for background effects in the radiographic image in state-of-the-art inspection systems is already known to the extent that such background effects are caused by the variation in the dark signal and gain between the individual photodiodes that make up a linear-array radiation detector. Part of this variation is due to random differences in the properties of the diodes themselves, while another part is due to the different lengths of the ray paths which radiate fanlike from a localized radiation source to the individual photodiodes. According to the inverse-square law, the shorter the ray path from the radiation source to a given sensor diode, the stronger the radiation received by that diode. In order to create a uniform image across the scanned area, the effect of these variations is cancelled through a so-called radiation detector calibration or radiation detector normalization.

In the first of two steps of the radiation detector calibration, the dark signals of the individual photodiodes of the radiation detector array are determined by measuring their respective diode currents while the radiation source is turned off. The respective brightness values for the dark signal of each diode are stored in memory. Subsequently, in the operating mode of the inspection system, the stored dark-level value is subtracted from the signal of each diode, so that the dark level of each diode corresponds to a net signal of zero.

In the second step of the radiation detector calibration, the signals of the individual diodes of the radiation detector array are determined with the radiation source turned on and with nothing but the empty conveyor belt located in the raypath between the radiation source and the radiation detector. These signals represent the respective maximum brightness level for each individual diode. Each signal is digitized, the respective dark level value is subtracted, and the resultant net signal values are used to calculate and store normalizing factors for the individual diodes. As a result of the calibration, the normalized dark level signal values for all diodes will all be zero, and the maximum brightness levels of all photodiodes will all correspond to an identical normalized value, for example 255 if expressed in terms of an 8-bit binary number.

In the operating mode of the radiographic inspection system, the raw measurement value from each diode is first converted into a net value by subtracting the stored dark signal value, and then into a normalized value by multiplying the net value with the stored normalizing factor for the respective diode.

As the calibration is performed with the conveyor in place, the reduction in brightness due to the conveyor is automatically included in the normalized results, so that in the case of a conveyor belt, a constant gray-level background in the radiographic image which is caused by the radiographic absorption of the belt is already cancelled out in the normalized brightness values.

SUMMARY

A method is disclosed of operating a radiographic inspection system having a radiation source for emitting scanning rays, a radiation detector for receiving scanning rays and converting them into detector signals, a processor for generating a radiographic image based on the detector signals, and a modular conveyor chain having identical modular segments connected in a closed loop for transporting articles under inspection through a space that is traversed by the scanning rays, wherein each modular segment includes a registration feature, said method comprising: removing from the radiographic image a background image that is caused essentially by the conveyor chain modular segments and by factors inherent in the radiation detector; calibrating the removing in a calibration mode by: C1) acquiring digital calibration data through determination of dark signals of individual photodiodes of an array in the radiation detector by measuring respective diode currents while the radiation source is turned off, digitizing said diode currents and retaining said digital calibration data in a one-dimensional data array; C2) acquiring raw image data for one of the modular segments of the modular conveyor chain when empty, and retaining the raw image data in a first two-dimensional data array as a raw digital image of the one modular segment; and C3) digitally processing the data retained in steps C1) and C2) reflecting an influence of the radiation source and the radiation detector, and the image data for one of the modular segments into calibration data and storing said calibration data in a memory of the radiographic inspection system; wherein the method comprises inspecting in an inspection mode by: I1) acquiring a radiographic image as raw digital image data of the articles travelling on the modular conveyor chain, and retaining the raw digital image data in a second two-dimensional data array as a raw digital image of an article with a background of said section of the modular conveyor chain; and I2) arithmetically processing the raw digital image data, using the calibration data, into an output image without said background image; and wherein the method comprises: referencing a location (P) within any radiographic image to an underlying modular segment with a longitudinal registration coordinate (y) in a transport direction of the modular conveyor chain.

A radiographic inspection system is also disclosed, comprising: a radiation source for emitting scanning rays; a radiation detector configured as a photodiode array for receiving scanning rays and converting them into detector signals; a processor for generating a radiographic image based on the detector signals; and a modular conveyor chain with identical modular segments which is arranged between the radiation source and the radiation detector for transporting articles under inspection, wherein each of the identical modular segments includes a registration feature whereby a location (P) within the radiographic image will be referenced to a respective modular segment with a longitudinal registration coordinate (y) in a transport direction of the conveyor chain.

BRIEF DESCRIPTION OF THE DRAWINGS

Additional refinements, advantages and features of the present disclosure are described in more detail below with reference to exemplary embodiments illustrated in the drawings, in which:

FIG. 1 illustrates an exemplary radiographic inspection system with features to implement an exemplary method as disclosed herein;

FIG. 1A represents an enlarged detail of FIG. 1;

DETAILED DESCRIPTION

Figure 2A:
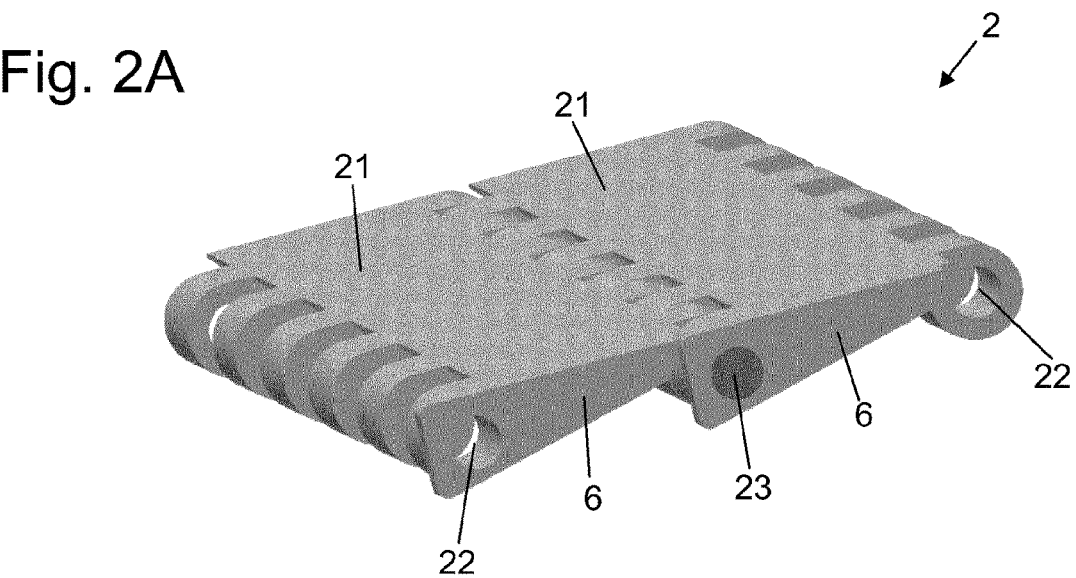
FIGS. 2A, 2B, 2C represent different views of a part of an exemplary conveyor chain in an exemplary radiographic inspection system according to the disclosure.

In view of limitations of a radiographic inspection system with a conveyor chain according to US 2012/0128133 A1, and further in view of the fact that the state of the art already offers a method of cancelling the background image in inspection systems with known belt conveyors through a calibration procedure, the present disclosure is directed to a method and a radiographic inspection system with a developed calibration mode capable of cancelling the background image in an inspection system with a modular conveyor chain.

Exemplary methods according to the disclosure can be used in a radiographic inspection system with a radiation source emitting scanning rays, with a radiation detector receiving the scanning rays and converting them into detector signals, with a processor generating a radiographic image based on the radiation detector signals, and with a modular conveyor chain with identical modular segments that are connected in a closed loop wherein each modular segment includes a registration feature, wherein articles under inspection are transported on the modular conveyor chain through a space that is traversed by the scanning rays. In accordance with the disclosure, an exemplary method accomplishes the task of removing from the radiographic image a background image that is caused essentially by the conveyor chain segments and by factors inherent in the radiation detector. As a result, an output image is obtained which shows the articles under inspection without the interfering background image of the conveyor chain.

In essence, an exemplary method as disclosed herein encompasses two operating modes of the radiographic inspection system: a calibration mode and an inspection mode.

In an exemplary calibration mode, data reflecting an influence of the radiation source and the radiation detector as well as image data for one of the modular segments are acquired by the radiographic inspection system and digitally processed into calibration data which are then stored in a memory of the radiographic inspection system.

This involves acquiring digital calibration data through determination of the dark signals of the individual photodiodes of the radiation detector array by measuring their respective diode currents while the radiation source is turned off, digitizing the diode current and retaining the digital calibration data in a one-dimensional data array, acquiring raw image data for one of the modular segments of the empty conveyor and retaining the raw image data in a first two-dimensional data array as a raw digital image of the modular segment and digitally processing the data retained in the foregoing steps.

In an exemplary inspection mode, the radiographic image of the articles under inspection with the background of the conveyor chain is acquired by the radiographic inspection system in the form of raw digital image data and the raw digital image data are retained in a second two-dimensional data array as a raw digital image of the article with the background of said section of the conveyor chain. The raw image data are arithmetically processed with the help of the previously stored calibration data into a clearer output image without the interfering background of the conveyor chain.

In order to be able to geometrically correlate the raw image data collected in the inspection mode to the calibration data collected and stored in the calibration mode, each modular segment includes a registration feature whereby a location within any radiographic image is referenced to the underlying modular segment with a longitudinal registration coordinate y in a transport direction of the conveyor chain.

An exemplary method as disclosed herein can take advantage of the fact that the conveyor chain is constituted by an endless loop of identical modular segments. Therefore, it is sufficient in the calibration mode to acquire, process and store the data for any single one of the modular segments rather than to acquire the data for an entire chain with typically several hundred segments, which would take a commensurately greater amount of time for the calibration mode and could require a prohibitive amount of memory capacity for the calibration data.

In exemplary embodiments, a radiographic inspection system that can be operated in accordance with exemplary methods disclosed herein is equipped with a spatially concentrated radiation source and with a radiation detector constituted by a linear array of photodiodes that are spaced at a uniform distance from each other. The radiation source and the radiation detector face each other across the modular conveyor chain. The radiation source generates scanning rays which emanate as a fan-shaped planar bundle from the radiation source to the radiation detector. The spatial arrangement of the radiation source and the radiation detector is such that the fan-shaped radiation bundle and the linear array of photodiodes lie in a common scanning plane which, for example, runs substantially orthogonal to the travel direction of the conveyor chain. In another exemplary embodiment of an arrangement as disclosed herein, the radiation source can be positioned vertically above the conveyor chain and the radiation detector vertically below the conveyor chain.

Advantageously, due to the nature of the radiation detector as a linear array of photodiodes, a location within any radiographic image can be referenced in the transverse direction of the conveyor chain with a transverse registration coordinate x corresponding to the array position of the photodiode associated with that location within the radiographic image.

While the articles under inspection move on the conveyor chain through the scanning plane, the photodiode array is triggered by a continuous sequence of pulses generated either by an internal clock or by an encoder device, wherein the timing of the pulses can be synchronized with the movement of the conveyor chain so that the linear photodiode array is generating detection signals at uniformly spaced intervals. In an alternative exemplary embodiment, while the articles under inspection move through the scanning plane, the scanner radiation can be generated in a continuous sequence of discrete pulses, and the pulse frequency is coordinated with the speed of the conveyor chain so that the sequence of signals received by the radiation detector array can be translated into a pattern of raster dots with different brightness values.

For example, to synchronize the detection signals of the photodiode array with the movement of the conveyor chain, the pulses could be triggered at predetermined uniform intervals of the registration coordinate y, so that the timing of the detection signals would in effect be controlled by the aforementioned registration feature.

For example, every time the linear array of photodiodes receives a trigger pulse, it produces a line of image dots of the radiographic image, and the entire sequential stream of trigger pulses results in a continuous raster-shaped image of the objects traveling on the conveyor chain as well as of the conveyor chain itself, wherein every image dot is spatially referenced by x- and y-registration coordinates as already described. The image itself results from the different respective levels of brightness of the image dots in the raster. The brightness of an image dot is for example, expressed as a brightness value in digital form. Consequently, the data set that characterizes an image dot contains the registration coordinates and the brightness level of the image dot.

In a system where a radiographic image is formed in accordance with the foregoing description, exemplary factors that determine the brightness levels of the individual image dots are:

the individually different dark signal and different radiation sensitivity of each photodiode in the radiation detector array;

the individually different distance of each photodiode from the radiation source;

the individually different amount of radiation intensity lost along the ray path from the radiation source to each photodiode due to absorption in the conveyor chain; and the individually different amount of radiation intensity lost along the ray path from the radiation source to each photodiode due to absorption in an article under inspection.

Accordingly, in a first step of an exemplary calibration mode of a method according to the disclosure, the radiation source is turned off and a diode current is measured for each diode in the radiation detector array. The diode current signal is digitized and stored in memory together with the transverse registration coordinate x as the dark signal $D(x)$ of the respective diode.

In a second step of an exemplary calibration mode, the radiation source is emitting radiation, the radiation detector receives trigger pulses to generate detection signals, and the conveyor chain is in motion. Image data for one segment of the empty conveyor chain are acquired as an x/y array of raw brightness calibration values $RBC(x,y)$. A net brightness calibration value $NBC(x,y)$ is calculated for each x/y location of the array by subtracting the dark signal $D(x)$ from the raw brightness calibration value $RBC(x,y)$. The reciprocal value $1/NBC(x,y)$ (or a multiple $k/NBC(x,y)$, wherein k is an arbitrarily selected normalization factor) is stored as brightness calibration factor $C(x,y)$ for the respective x/y location.

In an exemplary inspection mode, the raw image data for the conveyor chain with the articles under inspection are acquired as a continuous stream of raw brightness values, each of which can be (e.g., immediately) converted into a normalized output value by first subtracting the dark signal $D(x)$ for the respective photodiode and then multiplying the resultant net brightness value with the calibration factor $C(x,y)$ for the respective location. The normalized output values can be made available for display and/or further processing and as a result, while the articles under inspection travel through the plane formed by the scanning rays, a continuous raster image is formed in which the articles under inspection can be seen without the background image of the conveyor chain.

An exemplary radiographic inspection system in which a method according to the foregoing description can be implemented includes a radiation source emitting scanning rays, a radiation detector in the form of a photodiode array receiving the scanning rays and converting them into detector signals, a processor generating a radiographic image based on the detector signals, and a modular conveyor chain with identical modular segments which is arranged between the radiation source and the radiation detector and serves to transport articles under inspection, wherein each of the identical modular segments includes a registration feature whereby a location within the radiographic image can be referenced to the underlying modular segment of the location with a longitudinal registration coordinate y in a transport direction of the conveyor chain.

In an exemplary embodiment of the radiographic inspection system, the registration feature is realized as a ramp-shaped lateral border portion formed on the modular segment, wherein the radiation is passing through the ramp-shaped registration feature. This can be advantageous, as use can be made of the radiation already in place.

Alternatively, the registration feature can also be implemented as an optical sensor, a laser sensor, a magnetic induction sensor, a magnetic profile sensor, a toothed ruler section formed on the modular segment or as an encoded circular timing pattern connected to a sprocket drive of the conveyor chain, or any other suitable feature for achieving the functions disclosed herein.

In exemplary embodiments of a radiographic inspection system according to the disclosure, the radiation emitted by the radiation source is in the spectral range of X-rays, while the photodiodes of the radiation detector have a spectral sensitivity that is greatest for light with a longer wavelength than X-rays. The photodiodes are therefore, for example, covered with a layer of fluorescent material which serves to convert the X-rays into light of a wavelength matched to the spectral sensitivity of the photodiodes.

FIGS. 1 and 1A illustrate an exemplary radiographic inspection system 1 of a suitable configuration to carry out a method according to the disclosure. The principle elements of the radiographic inspection system 1 are the modular conveyor chain 2 (shown in cross-section with its transport direction oriented towards the viewer, with an article 3 being transported on the conveyor chain 2), a radiation source 4, a radiation detector 5 with a linear photodiode array 7, and a ramp-shaped registration feature 6 as shown by way of exemplary embodiments in detail in FIGS. 2A, 2B and 2C. The radiation source 4 generates scanning rays which emanate as a fan-shaped planar bundle from the radiation source 4 to the photodiode array 7 of the radiation detector 5. A segment 8 of the fan of imaging rays passes through the article 3, and a segment 9 of the imaging rays passes through the ramp-shaped registration feature 6. The signals produced by the photodiodes in the array 7 in response to one trigger pulse are converted by a computer or processor (not shown in the drawing) of the radiographic inspection system 1 into a line of image dots of a raster-shaped radiographic image representing the modular conveyor chain 2 and the articles 3 being transported on it. As the conveyor chain 2 with the articles 3 is continuously moving, each trigger pulse received by the radiation detector 5 produces a new line of the raster-shaped radiographic image.

Figure 2B:
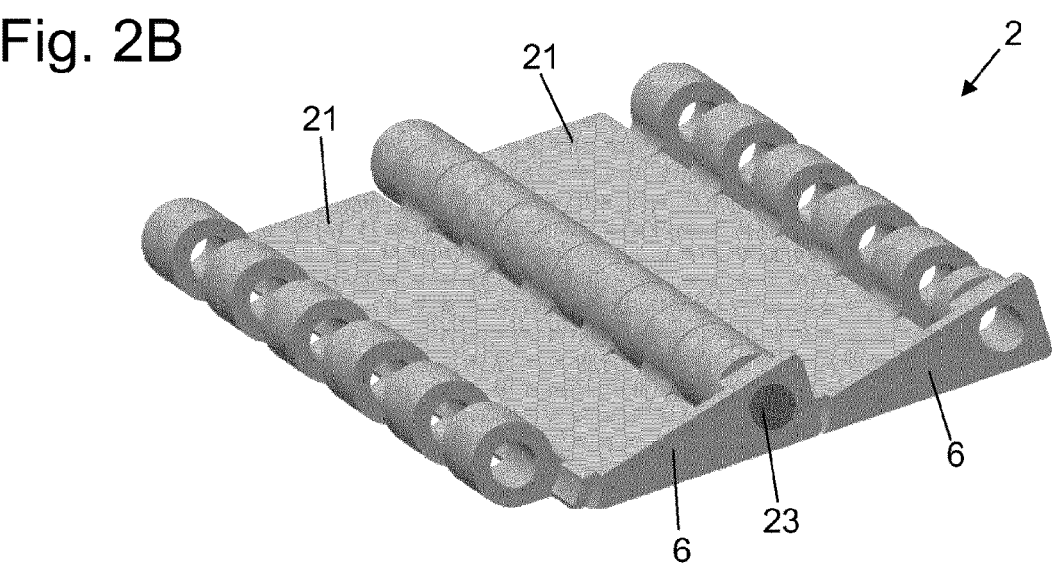
Figure 2C:
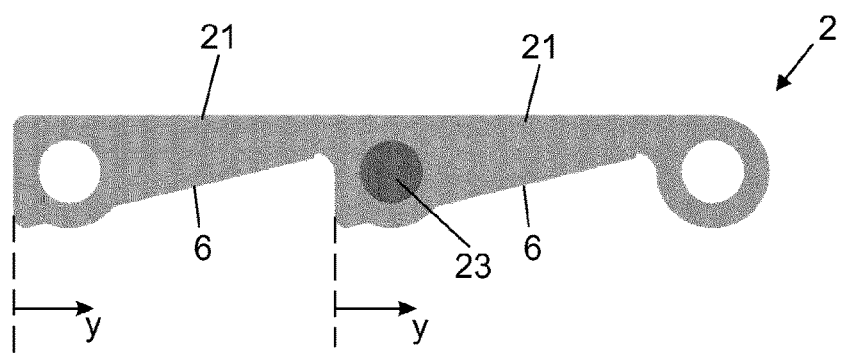

FIG. 2A shows two exemplary segments 21 of the modular conveyor chain 2 in a perspective view directed at the transport surface of the conveyor chain 2, while FIG. 2B represents a perspective view directed at the underside and FIG. 2C represents a side view of the conveyor chain segments 21. The segments 21 are connected to each other by hinges 22 which can extend over the entire width of the conveyor chain 2. A hinge pin 23 is for example, made of the same material as the segments. Each segment 21 has a registration feature 6 in the form of a ramp-shaped lateral border portion 6. Since the height h of the ramp-shaped lateral border 6 is a linear function of the distance y from the end of the chain segment, the registration coordinate y for any location P on the modular chain segment 2 and on the radiographic image (see FIGS. 3A-C) can be established by way of the associated height h of the border portion 6.

Figure 3A:
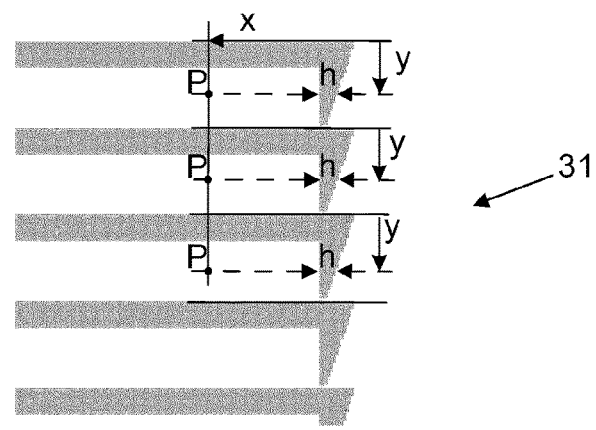
FIGS. 3A, 3B, 3C represent radiographic images of: (A) an empty conveyor chain, (B) an article under inspection with the background of the conveyor chain, and (C) an article under inspection wherein the background has been removed in accordance with an exemplary method of the present disclosure.

FIG. 3A represents an exemplary radiographic image 31 of the empty conveyor chain 2 of FIGS. 2A-C as it would appear for example in the inspection system 1 of FIG. 1, if a known method of radiation detector normalization were used instead of a background-cancellation method according to the present disclosure. The heavy hinge portions 22 of the segments 21 of the conveyor chain 2 appear as dark parallel stripes, and the border portions 6 appear as dark triangles. A location P with its registration coordinates x, y and the associated height h of the triangular border image is shown to illustrate the linear relationship between h and y, whereby the y-coordinate of P can be established by determining h. As is evident from the drawing, analogous locations P with identical x- and y-registration coordinates can repeat themselves continuously from one segment of the modular conveyor chain 2 to the next.

Figure 3B:
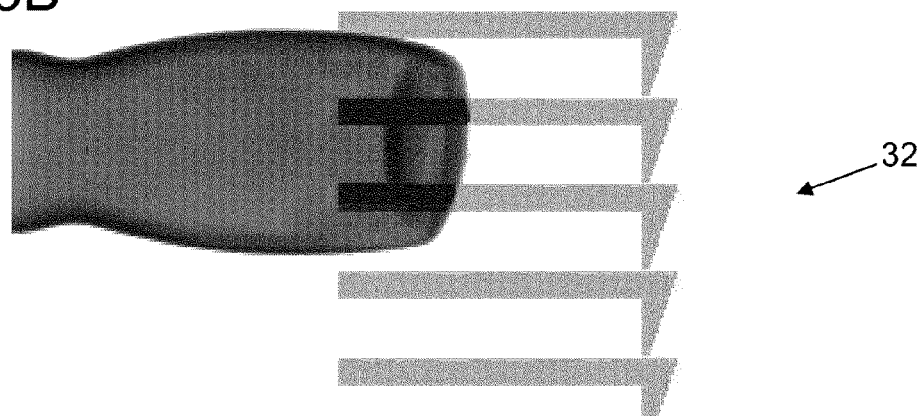

FIG. 3B represents an exemplary radiographic image 32 of the conveyor chain 2 with an article 3, again as it would appear in the inspection system 1 of FIG. 1, if a known method of radiation detector normalization were used instead of the background-cancellation method according to the disclosure. The dark image of the article 3 appears superimposed on the background image of the segments 21 of the conveyor chain 2.

Figure 3C:
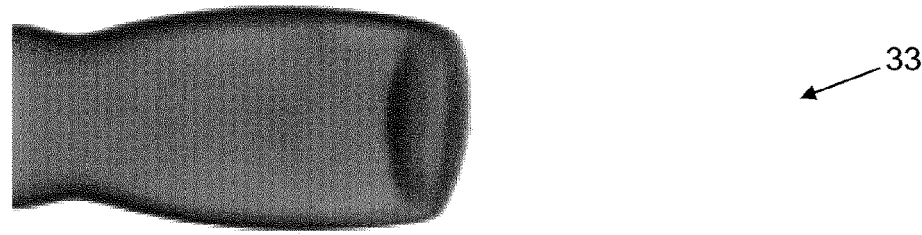

FIG. 3C represents an exemplary the output image 33 which the radiographic inspection system 1 will generate of the same article 3 and conveyor chain 2 if an exemplary signal-processing method according to the disclosure is used. As the striped background image of the conveyor chain segments 21 has been cancelled, the output image 33 of the article 3 is free of the interfering background.

Although the disclosure has been described through the presentation of specific examples of embodiments, it will be evident to those skilled in the art that numerous further variant embodiments could be developed from the teachings of the present disclosure, for example by combining the features of the individual examples with each other and/or by interchanging individual functional units between the embodiments described herein. For example the inventive concept is applicable to radiation of any wavelength that can—at least partially—be transmitted by an object under inspection and or the conveyor chain. A radiation detector other than a linear photodiode array, such as 2D-format radiation detector, for example area photodiode arrays, image intensifiers, flat panel imaging plates scintillation screen and camera etc. can be applied, wherein the registration feature and its mode of operation are slightly modified. It goes without saying that any such variant embodiments are considered to be part of the present disclosure.

Thus, it will be appreciated by those skilled in the art that the present disclosure can be embodied in other specific forms without departing from the spirit or essential characteristics thereof. The presently disclosed embodiments are therefore considered in all respects to be illustrative and not restricted. The scope of the disclosure is indicated by the appended claims rather than the foregoing description and all changes that come within the meaning and range and equivalence thereof are intended to be embraced therein.

LIST OF REFERENCE NUMERALS 1 radiographic inspection system
2 modular conveyor chain
3 article under inspection
4 radiation source
5 radiation detector
6 registration feature
7 linear array of photodiodes
8 fan segment of rays passing through 3
9 fan segment of rays passing through 6
21 segment of modular conveyor chain 2
22 hinge connecting segments 21
23 hinge pin
x transverse registration coordinate
y longitudinal registration coordinate
P location within radiographic image, image dot

What is claimed is:

1. A method of operating a radiographic inspection system having a radiation source for emitting scanning rays, a radiation detector for receiving the scanning rays and converting them into detector signals, a processor for generating a radiographic image based on the detector signals, and a modular conveyor chain having identical modular segments connected in a closed loop for transporting articles under inspection through a space that is traversed by the scanning rays, wherein each modular segment includes a registration feature, said method comprising:

removing from the radiographic image a background image that is caused essentially by the conveyor chain modular segments and by factors inherent in the radiation detector;

calibrating the removing in a calibration mode by:

C1) acquiring digital calibration data through determination of dark signals of individual photodiodes of an array in the radiation detector by measuring respective diode currents while the radiation source is turned off, digitizing said diode currents and retaining said digital calibration data in a one-dimensional data array;

C2) acquiring raw image data for one of the modular segments of the modular conveyor chain when empty, and retaining the raw image data in a first two-dimensional data array as a raw digital image of the one modular segment; and C3) digitally processing the data retained in steps C1) and C2) reflecting an influence of the radiation source and the radiation detector, and the image data for one of the modular segments into calibration data and storing said calibration data in a memory of the radiographic inspection system;

wherein the method comprises inspecting in an inspection mode by:

I1) acquiring a radiographic image as raw digital image data of the articles travelling on the modular conveyor chain, and retaining the raw digital image data of the articles in a second two-dimensional data array as a raw digital image of an article with a background of a section of the modular conveyor chain; and I2) arithmetically processing the raw digital image data of the article, using the calibration data, into an output image without said background image;

and wherein the method comprises:

referencing a location (P) within any radiographic image to an underlying modular segment with a longitudinal registration coordinate (y) in a transport direction of the modular conveyor chain.

2. The method of claim 1, wherein the radiation source is of a spatially concentrated configuration and the radiation detector includes a linear array of photodiodes arranged at regular intervals, said radiation source and said radiation detector facing each other across the modular conveyor chain, wherein the method comprises:

emanating scanning rays as a fan-shaped planar bundle from the radiation source to the radiation detector, said fan-shaped planar bundle and said linear array of photodiodes lying in a common scanning plane which runs substantially orthogonal to the transport direction of the modular conveyor chain.

3. The method of claim 2, comprising:

referencing a location (P) within any radiographic image in a transverse direction of the modular conveyor chain with a transverse registration coordinate (x) corresponding to an array position (x) of a photodiode associated with said location.

4. The method of claim 3, comprising:

while the articles under inspection move on the conveyor chain through the scanning plane, generating scanner radiation by the radiation source in a continuous stream of radiation while the radiation detector is triggered by pulses to generate detector signals, wherein timing of the pulses is synchronized with movement of the conveyor chain so that times when the fan-shaped planar bundle of radiation is converted into an output signal of the radiation detector correspond to uniform travel intervals of the modular conveyor chain and the articles being transported on it.

5. The method of claim 4, comprising:

converting radiation received by the photodiodes of the radiation detector at each individual trigger pulse into a line of substantially equidistant image dots, a sequence of trigger pulses causing a series of substantially equidistant parallel lines of image dots to be generated, so that said lines of image dots form the radiographic image as a raster of lines and columns of image dots, wherein each line of image dots is associated with a trigger pulse occurring at a given point in time and each column of image dots is associated with a specific photodiode in the linear array of photodiodes, wherein each image dot is spatially referenced by registration coordinates (x,y) against an underlying modular segment of the modular conveyor chain, and wherein each image dot is individually characterized by a level of brightness expressed in digital form as a brightness value.

6. The method of claim 2, comprising:

while the articles under inspection move on the conveyor chain through the scanning plane, generating scanner radiation by the radiation source in a continuous stream of radiation while the radiation detector is triggered by pulses to generate detector signals, wherein timing of the pulses is synchronized with movement of the conveyor chain so that times when the fan-shaped planar bundle of radiation is converted into an output signal of the radiation detector correspond to uniform travel intervals of the modular conveyor chain and the articles being transported on the modular conveyor chain.

7. The method of claim 6, comprising:

effecting synchronization between the trigger pulses and the movement of the conveyor chain by generating the trigger pulses at predetermined uniform intervals of the registration coordinate (y), so that the timing of the trigger pulses is controlled by a registration feature.

8. The method of claim 7, comprising:

converting radiation received by the photodiodes of the radiation detector at each individual trigger pulse into a line of substantially equidistant image dots, a sequence of trigger pulses causing a series of substantially equidistant parallel lines of image dots to be generated, so that said lines of image dots form the radiographic image as a raster of lines and columns of image dots, wherein each line of image dots is associated with a trigger pulse occurring at a given point in time and each column of image dots is associated with a specific photodiode in the linear array of photodiodes, wherein each image dot is spatially referenced by registration coordinates (x,y) against an underlying modular segment of the modular conveyor chain, and wherein each image dot is individually characterized by a level of brightness expressed in digital form as a brightness value.

9. The method of claim 6, comprising:

converting radiation received by the photodiodes of the radiation detector at each individual trigger pulse into a line of substantially equidistant image dots, a sequence of trigger pulses causing a series of substantially equidistant parallel lines of image dots to be generated, so that said lines of image dots form the radiographic image as a raster of lines and columns of image dots, wherein each line of image dots is associated with a trigger pulse occurring at a given point in time and each column of image dots is associated with a specific photodiode in the linear array of photodiodes, wherein each image dot is spatially referenced by registration coordinates (x,y) against an underlying modular segment of the modular conveyor chain, and wherein each image dot is individually characterized by a level of brightness expressed in digital form as a brightness value.

10. The method of claim 9, wherein the brightness level of an image dot is determined by:

an individually different dark signal and light sensitivity of each photodiode in the radiation detector;
an individually different distance of each photodiode from the radiation source;
an individually different amount of radiation intensity lost along a ray path from the radiation source to each photodiode due to absorption in the modular conveyor chain; and
an individually different amount of radiation intensity lost along the ray path from the radiation source to each photodiode due to absorption in an article under inspection.

11. The method of claim 1, wherein in the calibration mode, the acquiring image data for one of the modular segments comprises:
turning the radiation source on and setting the modular conveyor chain in motion;
acquiring image data for one segment of the conveyor chain when empty as an (x,y)-array of raw brightness calibration values RBC(x,y);
calculating net brightness calibration values NBC(x,y) for each (x,y)-location by subtracting a dark signal D(x) from each raw brightness calibration value RBC(x,y);
calculating a brightness calibration factor C(x,y)=k/NBC(x,y); and
storing the brightness calibration factor in a memory array C(x,y).

12. The method of claim 11, wherein in the inspection mode, the acquiring a radiographic image as raw digital image data of the articles travelling on the modular conveyor chain comprises:
acquiring the radiographic image of the articles with the underlying background of the modular conveyor chain as image dots (P);
referencing each image dot (P) to the underlying background by way of registration coordinates (x,y); and
digitizing the brightness level of each image dot (P) into a raw brightness value RBV(x,y).

13. The method of claim 12, wherein in the inspection mode, the arithmetically processing the raw digital image data into an output image without the background image comprises:
subtracting the dark signal D(x) from the raw brightness value RBV(x,y) to produce a net brightness value NBV(x,y);
calculating a normalized brightness value CBV(x,y)=C(x,y)×NBV(x,y); and
adding a new raster dot with a normalized brightness value CBV(x,y) to a continuous output image of the radiographic inspection system.

14. A radiographic inspection system, comprising:
a radiation source for emitting scanning rays;
a radiation detector configured as a photodiode array for receiving scanning rays and converting them into detector signals;
a processor configured to generate a radiographic image based on the detector signals; and
a modular conveyor chain with identical modular segments connected in a closed loop, the modular conveyor chain being arranged between the radiation source and the radiation detector for transporting articles under inspection through a space that is traversed by the scanning rays, wherein each of the identical modular segments includes a registration feature whereby a location (P) within the radiographic image will be referenced to a respective modular segment with a longitudinal registration coordinate (y) in a transport direction of the conveyor chain,
the radiographic inspection system being configured to:
remove from the radiographic image a background image that is caused essentially by the conveyor chain modular segments and by factors inherent in the radiation detector,
calibrate the removing in a calibration mode of the radiographic inspection system by:
C1) acquiring digital calibration data through determination of dark signals of individual photodiodes of an array in the radiation detector by measuring respective diode currents while the radiation source is turned off, digitizing said diode currents and retaining said digital calibration data in a one-dimensional data array;
C2) acquiring raw image data for one of the modular segments of the modular conveyor chain when empty, and retaining the raw image data in a first two-dimensional data array as a raw digital image of the one modular segment; and
C3) digitally processing the data retained in steps C1) and C2) reflecting an influence of the radiation source and the radiation detector, and the image data for one of the modular segments into calibration data and storing said calibration data in a memory of the radiographic inspection system,
inspect in an inspection mode of the radiographic inspection system by:
I1) acquiring a radiographic image as raw digital image data of the articles travelling on the modular conveyor chain, and retaining the raw digital image data of the articles in a second two-dimensional data array as a raw digital image of an article with a background of a section of the modular conveyor chain; and
I2) arithmetically processing the raw digital image data of the article, using the calibration data, into an output image without said background image, and
reference a location (P) within any radiographic image to an underlying modular segment with a longitudinal registration coordinate (y) in a transport direction of the modular conveyor chain.

15. The radiographic inspection system of claim 14, wherein the registration feature comprises:
a ramp-shaped lateral border portion formed on a respective modular segment.

16. The radiographic inspection system of claim 15, wherein the radiation source comprises:
an X-ray source, and wherein photodiodes of the photodiode array have a spectral sensitivity that is greatest for light with a wavelength longer than that of X-rays, the photodiodes including a fluorescent coating for converting X-rays into light of a wavelength matched to a spectral sensitivity of the photodiodes.

17. The radiographic inspection system of claim 14, wherein the registration feature comprises:
a toothed ruler section formed on a respective modular segment.

18. The radiographic inspection system of claim 14, wherein the registration feature comprises:
an encoded circular timing pattern connected to a sprocket drive of the modular conveyor chain.

19. The radiographic inspection system of claim 18, wherein the radiation source comprises:

an X-ray source, and wherein photodiodes of the photodiode array have a spectral sensitivity that is greatest for light with a wavelength longer than that of X-rays, the photodiodes including a fluorescent coating for converting X-rays into light of a wavelength matched to a spectral sensitivity of the photodiodes.

20. The radiographic inspection system of claim 14, wherein the radiation source comprises:
an X-ray source, and wherein photodiodes of the photodiode array have a spectral sensitivity that is greatest for light with a wavelength longer than that of X-rays, the photodiodes including a fluorescent coating for converting X-rays into light of a wavelength matched to a spectral sensitivity of the photodiodes.

* * * * *